United States Patent [19]

Johnson

[11] 4,216,336
[45] Aug. 5, 1980

[54] 5-KETO PROSTAGLANDINS
[75] Inventor: Roy A. Johnson, Kalamazoo, Mich.
[73] Assignee: The Upjohn Company, Kalamazoo, Mich.
[21] Appl. No.: 51,223
[22] Filed: Jun. 22, 1979

Related U.S. Application Data

[60] Division of Ser. No. 932,898, Aug. 11, 1978, which is a division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.² ............................................ C07C 177/00
[52] U.S. Cl. ..................................... 560/53; 562/463
[58] Field of Search ........................... 560/53; 562/463

[56] References Cited
PUBLICATIONS

Derwent Abstract 29303A/16 J53023-954 06.03.78.
Derwent Abstract 29302/A16 J53023-953 06.03.78.
Chem. Abst. 87:200908k Tanaka 02.03.77.

Primary Examiner—Paul J. Killos
Attorney, Agent, or Firm—Robert A. Armitage; Morris L. Nielsen

[57] ABSTRACT

Prostaglandin $F_1\alpha$ ($PGF_1\alpha$) derivatives having a 5-keto feature, for example

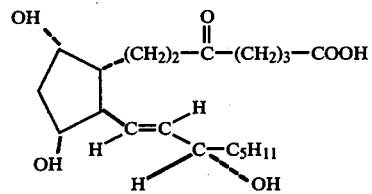

said derivatives having pharmacological activity. Processes for preparing them and the appropriate intermediates are disclosed.

117 Claims, No Drawings

5-KETO PROSTAGLANDINS

CROSS REFERENCE TO RELATED APPLICATIONS

This application is a division of copending application Ser. No. 932,898 filed Aug. 11, 1978, which was a division of then copending application Ser. No. 819,856 filed July 28, 1977, now issued as U.S. Pat. No. 4,123,441, which was a continuation-in-part of then copending application Ser. No. 725,546, filed Sept. 22, 1976, since abandoned, which was a continuation-in-part of then copending application Ser. No. 716,960, filed Aug. 23, 1976, since abandoned.

BACKGROUND OF THE INVENTION

This invention relates to prostaglandin derivatives and to a process for preparing them.

The prostaglandins and analogs are well-known organic compounds derived from prostanoic acid which has the following structure and atom numbering:

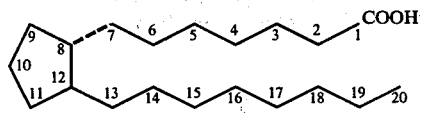

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol. Rev. 20, 1 (1968). For related compounds see Pace-Asciak et al., Biochem. 10, 3657 (1971). Related compounds are described in a publication on 6-ketone-prostaglandin F$_{1\alpha}$ by Pace-Asciak, J. Am. Chem. Soc. 98, 2348 (1976) and a publication on "PGX" (6,9α-oxido-9α,15α-dihydroxyprosta-(Z)5, (E)13-dienoic acid) by E. J. Corey et al., J. Am. Chem. Soc. 99, 20006 (1977).

The essential material for this application, including the background of the invention, the disclosure of the invention, and the description of the preferred embodiments, including Preparations and Examples, is incorporated by reference from issued U.S. Pat. No. 4,123,441 under the provisions of M.P.E.P. 608.01(p).

SUMMARY OF THE INVENTION

It is the purpose of this invention to provide novel products having pharmacological activity. It is a further purpose to provide processes for preparing these products and their intermediates.

Accordingly, there is provided a compound of the formula:

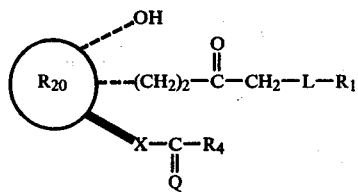

or a mixture comprising that compound and the enantiomer thereof wherein R$_{20}$ is

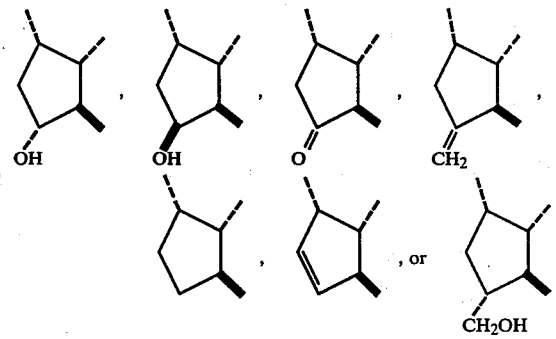

wherein L is
(1) —(CH$_2$)$_d$—C(R$_2$)$_2$—
(2) —O—CH$_2$—Y— or
(3) —CH=CH—
  wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is

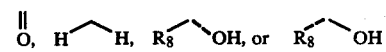

wherein R$_8$ is hydrogen or alkyl of one to 4 carbon atoms, inclusive,
wherein R$_1$ is
(1) —COOR$_3$
(2) —CH$_2$OH
(3) —CH$_2$N(R$_9$)(R$_{18}$)
(4)

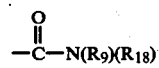

or
(5)

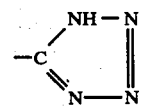

wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

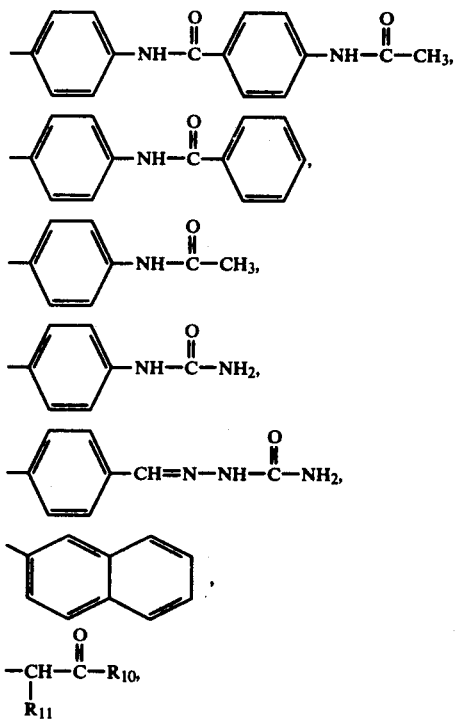

(g)

(h)

(i)

(j)

(k)

(l)

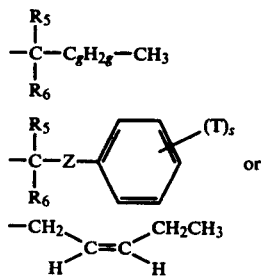

(m)

wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein $R_4$ is $$-\overset{R_5}{\underset{R_6}{C}}-C_gH_{2g}-CH_3 \quad (1)$$

$$-\overset{R_5}{\underset{R_6}{C}}-Z-\underset{}{\bigcirc}(T)_s \quad \text{or} \quad (2)$$

$$-CH_2\overset{}{\underset{H}{C}}=C\overset{CH_2CH_3}{\underset{H}{}} \quad (3)$$

wherein $C_gH_{2g}$ is is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring: wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH=CH—
(2) cis—CH=CH—
(3) —C≡C— or
(4) —CH$_2$CH$_2$—;

including the lower alkanoates thereof.

In formula 1 as used herein, attachment to $\textcircled{R_{20}}$ corresponds to bonds to the cyclopentane ring at the C-8, C-9, and C-12 positions following prostaglandin nomenclature, thus:

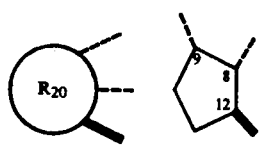

Within the scope of the prostaglandin derivatives described herein there are represented (a) PGF$_\alpha$ compounds when $\textcircled{R_{20}}$ is

(b) 11β-PGF$_\alpha$ compounds when $\textcircled{R_{20}}$ is

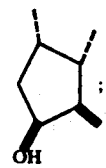

(c) 11-Deoxy-11-keto-PGF$_\alpha$ compounds when $\textcircled{R_{20}}$ is

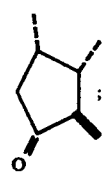

(d) 11-Deoxy-11-methylene-PGF$_\alpha$ compounds when $\textcircled{R_{20}}$ is

(e) 11-Deoxy-PGF$_\alpha$ compounds when $\textcircled{R_{20}}$ is (f) 11-Deoxy-10,11-Didehydro-PGF$_\alpha$ compounds when R$_{20}$ is

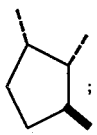

(g) 11-Deoxy-11-hydroxymethyl-PGF$_\alpha$ compounds when R$_{20}$ is

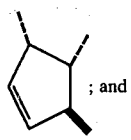

For those compounds of formula 1 wherein Q is

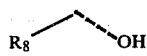

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formula 1 when Q is

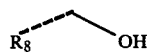

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

A typical example of the keto compounds of formula 1 is represented by the formula

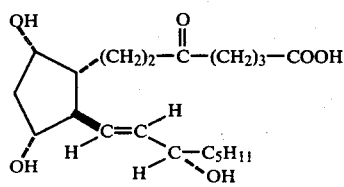

named 5-keto-PGF$_{1\alpha}$. The compound of formula V is a species of the formula-1 compounds wherein R$_{20}$ is

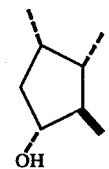

L is —(CH$_2$)$_2$—, Q is

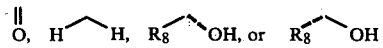

R$_1$ is —COOH, R$_4$ is n-pentyl, and X is trans—CH=CH—.

I claim:
1. A compound of the formula

$$R_{20}\text{—(CH}_2)_2\text{—}\overset{OH}{\underset{\underset{Q}{\overset{\|}{X-C}}-\underset{R_6}{\overset{R_5}{C}}-Z}{C}}\text{—CH}_2\text{—L—COOR}_3 \quad (T)_s$$

or a mixture comprising that compound and the enantiomer thereof wherein R$_{20}$ is

wherein L is
(1) —(CH$_2$)$_d$—C(R$_2$)$_2$—
(2) —O—CH$_2$—Y or
(3) —CH=CH—
   wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is $$\overset{\|}{O},\ H\diagdown OH,\ R_8\diagdown OH,\ or\ R_8\diagdown OH$$

wherein R$_8$ is hydrogen or alkyl of one to 4 carbon atoms, inclusive,
wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

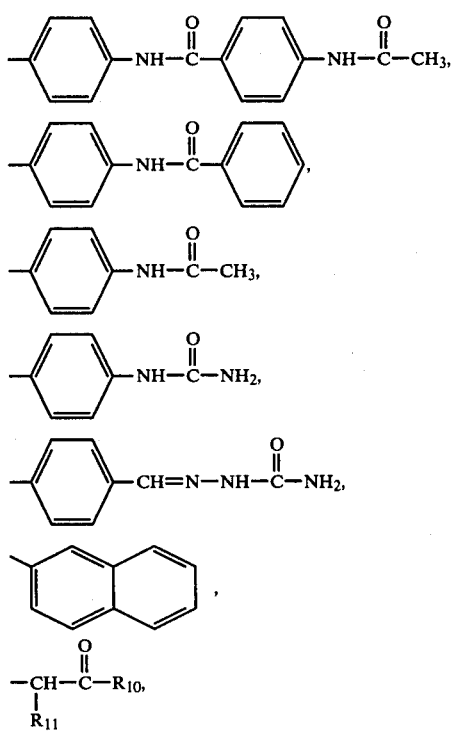

wherein R₁₀ is phenyl, p-bromophenyl, p-biphenyl, p-nitrophenyl, p-benzamidophenyl, or 2-naphthyl, and wherein R₁₁ is hydrogen or benzoyl, or (n) a pharmacologically acceptable cation, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro when Z is oxa (—O—);

wherein Z represents an oxa atom (—O—) or CjH₂j wherein CjH₂j is a valence bond or alkylene of one to 9 carbon atoms, inclusive, with one to 6 carbon atoms, inclusive between CR₅R₆— and the phenyl ring;

wherein T is alkyl of one to 4 carbon atoms, inclusive, fluoro, chloro, trifluoromethyl, or —OR₇— wherein R₇ is alkyl of one to 4 carbon atoms, inclusive, and s is zero, one, 2 or 3, with the proviso that not more than two T's are other than alkyl and when s is 2 or 3 the T's are either the same or different; and wherein X is
(1) trans—CH═CH—
(2) cis—CH═CH—
(3) —C≡C— or
(4) —CH₂CH₂—;
including the lower alkanoates thereof.

2. A compound according to claim 1 wherein R₂₀ is

3. A compound according to claim 1 wherein R₂₀ is

4. A compound according to claim 1 wherein R₂₀ is

5. A compound according to claim 1 wherein R₂₀ is

6. A compound according to claim 1 wherein R₂₀ is

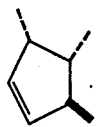

7. A compound according to claim 1 wherein R₂₀ is

8. A compound according to claim 1 wherein R₂₀ is

9. A compound according to claim 8 wherein L is —(CH₂)d—CH₂—, d being zero to 5, and wherein Q is

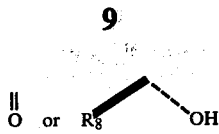

wherein R₈ is limited to hydrogen, methyl, or ethyl.

10. A compound according to claim 9 wherein R₅ and R₆ are hydrogen.

11. A compound according to claim 10 wherein X is trans—CH═CH—.

12. A compound according to claim 11 wherein R₃ is hydrogen, alkyl of one to 12 carbon atoms, inclusive, or a pharmacologically acceptable cation.

13. A compound according to claim 12 wherein R₃ is methyl.

14. 5-Keto-17-phenyl-18,19,20-trinor-PGF$_{1\alpha}$, methyl ester, a compound according to claim 13.

15. 5-Keto-17-(m-trifluoromethylphenyl)-18,19,20-trinor-PGF$_{1\alpha}$, methyl ester, a compound according to claim 13.

16. 5-Keto-17-(m-chlorophenyl)-18,19,20-trinor-PGF$_{1\alpha}$, methyl ester, a compound according to claim 13.

17. 5-Keto-17-(p-chlorophenyl)-18,19,20-trinor-PGF$_{1\alpha}$, methyl ester, a compound according to claim 13.

18. 5-Keto-16-phenoxy-17,18,19,20-tetranor-PGF$_{1\alpha}$, methyl ester, a compound according to claim 13.

19. 5-Keto-16-(m-trifluoromethylphenoxy)-17,18,19,20-tetranor-PGF$_{1\alpha}$, methyl ester, a compound according to claim 13.

20. 5-Keto-16-(m-chlorophenoxy)-17,18,19,20-tetranor-PGF$_{1\alpha}$, methyl ester, a compound according to claim 13.

21. 5-Keto-16-(p-chlorophenoxy)-17,18,19,20-tetranor-PGF$_{1\alpha}$, methyl ester, a compound according to claim 13.

22. A compound according to claim 12 wherein R₃ is sodium.

23. 5-Keto-17-phenyl-18,19,20-trinor-PGF$_{1\alpha}$, sodium salt, a compound according to claim 22.

24. 5-Keto-17-(m-trifluoromethylphenyl)-18,19,20-trinor-PGF$_{1\alpha}$, sodium salt, a compound according to claim 22.

25. 5-Keto-17-(m-chlorophenyl)-18,19,20-trinor-PGF$_{1\alpha}$, sodium salt, a compound according to claim 22.

26. 5-Keto-17-(p-chlorophenyl)-18,19,20-trinor-PGF$_{1\alpha}$, sodium salt, a compound according to claim 22.

27. 5-Keto-16-phenoxy-17,18,19,20-tetranor-PGF$_{1\alpha}$, sodium salt, a compound according to claim 22.

28. 5-Keto-16-(m-trifluoromethylphenoxy)-17,18,19,20-tetranor-PGF$_{1\alpha}$, sodium salt, a compound according to claim 22.

29. 5-Keto-16-(m-chlorophenoxy)-17,18,19,20-tetranor-PGF$_{1\alpha}$, sodium salt, a compound according to claim 22.

30. 5-Keto-16-(p-chlorophenoxy)-17,18,19,20-tetranor-PGF$_{1\alpha}$, sodium salt, a compound according to claim 22.

31. A compound according to claim 10 wherein X is —C≡C—.

32. A compound according to claim 31 wherein R₃ is hydrogen, alkyl of one to 12 carbon atoms, inclusive, or a pharmacologically acceptable cation.

33. A compound according to claim 32 wherein R₃ is methyl.

34. 5-Keto-17-phenyl-18,19,20-trinor-13,14-didehydro-PGF$_{1\alpha}$, methyl ester, a compound according to claim 33.

35. 5-Keto-16-phenoxy-17,18,19,20-tetranor-13,14-didehydro-PGF$_{1\alpha}$, methyl ester, a compound according to claim 33.

36. A compound according to claim 32 wherein R₃ is sodium.

37. 5-Keto-17-phenyl-18,19,20-trinor-13,14-didehydro-PGF$_{1\alpha}$, sodium salt, a compound according to claim 36.

38. 5-Keto-16-phenoxy-17,18,19,20-tetranor-13,14-didehydro-PGF$_{1\alpha}$, sodium salt, a compound according to claim 36.

39. A compound according to claim 10 wherein X is —CH₂CH₂—.

40. A compound according to claim 39 wherein R₃ is hydrogen, alkyl of one to 12 carbon atoms, inclusive, or a pharmacologically acceptable cation.

41. A compound according to claim 40 wherein R₃ is methyl.

42. 5-Keto-17-phenyl-18,19,20-trinor-13,14-dihydro-PGF$_{1\alpha}$, methyl ester, a compound according to claim 41.

43. 5-Keto-17-(m-chlorophenyl)-18,19,20-trinor-13,14-dihydro-PGF$_{1\alpha}$, methyl ester, a compound according to claim 41.

44. 5-Keto-16-phenoxy-17,18,19,20-tetranor-13,14-dihydro-PGF$_{1\alpha}$, methyl ester, a compound according to claim 41.

45. 5-Keto-16-(m-trifluoromethylphenoxy)-17,18,19,20-tetranor-13,14-dihydro-PGF$_{1\alpha}$, methyl ester, a compound according to claim 41.

46. 5-Keto-16-(m-chlorophenoxy)-17,18,19,20-tetranor-13,14-dihydro-PGF$_{1\alpha}$, methyl ester, a compound according to claim 41.

47. A compound according to claim 40 wherein R₃ is sodium.

48. 5-Keto-17-phenyl-18,19,20-trinor-13,14-dihydro-PGF$_{1\alpha}$, sodium salt, a compound according to claim 47.

49. 5-Keto-17-(m-chlorophenyl)-18,19,20-trinor-13,14-dihydro-PGF$_{1\alpha}$, sodium salt, a compound according to claim 47.

50. 5-Keto-16-phenoxy-17,18,19,20-tetranor-13,14-dihydro-PGF$_{1\alpha}$, sodium salt, a compound according to claim 47.

51. 5-Keto-16-(m-trifluoromethylphenoxy)-17,18,19,20-tetranor-13,14-dihydro-PGF$_{1\alpha}$, sodium salt, a compound according to claim 47.

52. 5-Keto-16-(m-chlorophenoxy)-17,18,19,20-tetranor-13,14-dihydro-PGF$_{1\alpha}$, sodium salt, a compound according to claim 47.

53. A compound according to claim 9 wherein R₅ and R₆ are methyl.

54. A compound according to claim 53 wherein X is trans-CH═CH—.

55. A compound according to claim 54 wherein R₃ is hydrogen, alkyl of one to 12 carbon atoms, inclusive, or a pharmacologically acceptable cation.

56. A compound according to claim 55 wherein R₃ is methyl.

57. 5-Keto-16,16-dimethyl-17-phenyl-18,19,20-trinor-PGF$_{1\alpha}$, methyl ester, a compound according to claim 56.

58. 5-Keto-16-methyl-16-phenoxy-18,19,20-trinor-PGF$_{1\alpha}$, methyl ester, a compound according to claim 56.

59. A compound according to claim 55 wherein $R_3$ is sodium.

60. 5-Keto-16,16-dimethyl-17-phenyl-18,19,20-trinor-PGF$_{1\alpha}$, sodium salt, a compound according to claim 59.

61. 5-Keto-16-methyl-16-phenoxy-18,19,20-trinor-PGF$_{1\alpha}$, sodium salt, a compound according to claim 59.

62. A compound according to claim 53 wherein X is —C≡C—.

63. A compound according to claim 62 wherein $R_3$ is hydrogen, alkyl of one to 12 carbon atoms, inclusive, or a pharmacologically acceptable cation.

64. A compound according to claim 63 wherein $R_3$ is methyl.

65. 5-Keto-16-methyl-16-phenoxy-18,19,20-trinor-13,14-didehydro-PGF$_{1\alpha}$, methyl ester, a compound according to claim 64.

66. A compound according to claim 63 wherein $R_3$ is sodium.

67. 5-Keto-16-methyl-16-phenoxy-18,19,20-trinor-13,14-didehydro-PGF$_{1\alpha}$, sodium salt, a compound according to claim 66.

68. A compound according to claim 53, wherein X is —CH$_2$CH$_2$—.

69. A compound according to claim 68 wherein $R_3$ is hydrogen, alkyl of one to 12 carbon atoms, inclusive, or a pharmacologically acceptable cation.

70. A compound according to claim 69 wherein $R_3$ is methyl.

71. 5-Keto-16,16-dimethyl-17-phenyl-18,19,20-trinor-13,14-dihydro-PGF$_{1\alpha}$, methyl ester, a compound according to claim 70.

72. A compound according to claim 69 wherein $R_3$ is sodium.

73. 5-Keto-16,16-dimethyl-17-phenyl-18,19,20-trinor-13,14-dihydro-PGF$_{1\alpha}$, sodium salt, a compound according to claim 72.

74. A compound according to claim 9 wherein $R_5$ and $R_6$ are fluoro.

75. A compound according to claim 74 wherein X is trans—CH=CH—.

76. A compound according to claim 75 wherein $R_3$ is hydrogen, alkyl of one to 12 carbon atoms, inclusive, or a pharmacologically acceptable cation.

77. A compound according to claim 76 wherein $R_3$ is methyl.

78. 5-Keto-16,16-difluoro-17-phenyl-18,19,20-trinor-PGF$_{1\alpha}$, methyl ester, a compound according to claim 77.

79. A compound according to claim 76 wherein $R_3$ is sodium.

80. 5-Keto-16,16-difluoro-17-phenyl-18,19,20-trinor-PGF$_{1\alpha}$, sodium salt, a compound according to claim 79.

81. A compound according to claim 74 wherein X is —C≡C—.

82. A compound according to claim 81 wherein $R_3$ is hydrogen, alkyl of one to 12 carbon atoms, inclusive, or a pharmacologically acceptable cation.

83. A compound according to claim 82 wherein $R_3$ is methyl.

84. 5-Keto-16,16-difluoro-17-phenyl-18,19,20-trinor-13,14-didehydro-PGF$_{1\alpha}$, methyl ester, a compound according to claim 83.

85. A compound according to claim 82 wherein $R_3$ is sodium.

86. 5-Keto-16,16-difluoro-17-phenyl-18,19,20-trinor-13,14-didehydro-PGF$_{1\alpha}$, sodium salt, a compound according to claim 85.

87. A compound according to claim 8 wherein L is —(CH$_2$)$_d$—CF$_2$—, d being zero to 5, and wherein Q is

wherein $R_8$ is limited to hydrogen, methyl or ethyl.

88. A compound according to claim 87 wherein $R_5$ and $R_6$ are hydrogen.

89. A compound according to claim 88 wherein X is trans—CH=CH—.

90. A compound according to claim 89 wherein $R_3$ is hydrogen, alkyl of one to 12 carbon atoms, inclusive, or a pharmacologically acceptable cation.

91. A compound according to claim 90 wherein $R_3$ is methyl.

92. 5-Keto-2,2-difluoro-17-phenyl-18,19,20-trinor-PGF$_{1\alpha}$, methyl ester, a compound according to claim 91.

93. 5-Keto-2,2-difluoro-16-phenoxy-17,18,19,20-tetranor-PGF$_{1\alpha}$, methyl ester, a compound according to claim 91.

94. A compound according to claim 90 wherein $R_3$ is sodium.

95. 5-Keto-2,2-difluoro-17-phenyl-18,19,20-trinor-PGF$_{1\alpha}$, sodium salt, a compound according to claim 24.

96. 5-Keto-2,2-difluoro-16-phenoxy-17,18,19,20-tetranor-PGF$_{1\alpha}$, sodium salt, a compound according to claim 94.

97. A compound according to claim 88 wherein X is —C≡C—.

98. A compound according to claim 97 wherein $R_3$ is hydrogen, alkyl of one to 12 carbon atoms, inclusive, or a pharmacologically acceptable cation.

99. A compound according to claim 98 wherein $R_3$ is methyl.

100. 5-Keto-2,2-difluoro-16-phenoxy-17,18,19,20-tetranor-13,14-didehydro-PGF$_{1\alpha}$, methyl ester, a compound according to claim 99.

101. A compound according to claim 98 wherein $R_3$ is sodium.

102. 5-Keto-2,2-difluoro-16-phenoxy-17,18,19,20-tetranor-13,14-didehydro-PGF$_{1\alpha}$, sodium salt, a compound according to claim 101.

103. A compound according to claim 88, wherein X is —CH$_2$CH$_2$—.

104. A compound according to claim 103 wherein $R_3$ is hydrogen, alkyl of one to 12 carbon atoms, inclusive, or a pharmacologically acceptable cation.

105. A compound according to claim 104 wherein $R_3$ is methyl.

106. 5-Keto-2,2-difluoro-17-phenyl-18,19,20-trinor-13,14-dihydro-PGF$_{1\alpha}$, methyl ester, a compound according to claim 105.

107. A compound according to claim 104 wherein $R_3$ is sodium.

108. 5-Keto-2,2-difluoro-17-phenyl-18,19,20-trinor-13,14-dihydro-PGF$_{1\alpha}$, sodium salt, a compound according to claim 107.

109. A compound according to claim 87 wherein $R_5$ and $R_6$ are methyl.

110. A compound according to claim 109 wherein X is —CH$_2$CH$_2$—.

111. A compound according to claim 110 wherein $R_3$ is hydrogen, alkyl of one to 12 carbon atoms, inclusive, or a pharmacologically acceptable cation.

112. A compound according to claim 111 wherein $R_3$ is methyl.

113. 5-Keto-2,2-difluoro-16,16-dimethyl-17-phenyl-18,19,20-trinor-13,14-dihydro-PGF$_{1\alpha}$, methyl ester, a compound according to claim 112.

114. 5-Keto-2,2-difluoro-16-phenoxy-17,18,19,20-tetranor-13,14-dihydro-PGF$_{1\alpha}$, methyl ester, a compound according to claim 112.

115. A compound according to claim 111 wherein $R_3$ is sodium.

116. 5-Keto-2,2-difluoro-16,16-dimethyl-17-phenyl-18,19,20-trinor-13,14-dihydro-PGF$_{1\alpha}$, sodium salt, a compound according to claim 115.

117. 5-Keto-2,2-difluoro-16-phenoxy-17,18,19,20-tetranor-13,14-dihydro-PGF$_{1\alpha}$, sodium salt, a compound according to claim 115.

* * * * *